United States Patent
Lessing et al.

(10) Patent No.: US 10,172,602 B2
(45) Date of Patent: Jan. 8, 2019

(54) SOFT ROBOTIC RETRACTORS

(71) Applicant: Soft Robotics, Inc., Cambridge, MA (US)

(72) Inventors: Joshua Aaron Lessing, Cambridge, MA (US); Ryan Richard Knopf, Melrose, MA (US); Marc Graham, Somerville, MA (US); Carl Vause, Concord, MA (US)

(73) Assignee: SOFT ROBOTICS, INC., Bedford, MA (US)

( * ) Notice: Subject to any disclaimer, the term of this patent is extended or adjusted under 35 U.S.C. 154(b) by 0 days.

(21) Appl. No.: 16/034,677

(22) Filed: Jul. 13, 2018

(65) Prior Publication Data
US 2018/0325507 A1 Nov. 15, 2018

Related U.S. Application Data

(63) Continuation of application No. 14/937,554, filed on Nov. 10, 2015, now Pat. No. 10,028,734.

(60) Provisional application No. 62/079,302, filed on Nov. 13, 2014.

(51) Int. Cl.
*A61B 17/02* (2006.01)
*A61B 34/00* (2016.01)
*A61B 17/00* (2006.01)

(52) U.S. Cl.
CPC .......... *A61B 17/02* (2013.01); *A61B 17/0218* (2013.01); *A61B 34/70* (2016.02); *A61B 2017/00017* (2013.01); *A61B 2017/00557* (2013.01); *A61B 2017/0225* (2013.01)

(58) Field of Classification Search
CPC ............ A61B 17/02; A61B 2017/0225; A61B 17/0218
See application file for complete search history.

(56) References Cited

U.S. PATENT DOCUMENTS

| 5,400,773 A | 3/1995 | Zhu et al. |
| 5,865,728 A * | 2/1999 | Moll .................. A61B 17/0218 600/204 |
| 6,071,295 A * | 6/2000 | Takahashi .............. A61B 17/02 604/176 |

(Continued)

FOREIGN PATENT DOCUMENTS

| FR | 2726993 A1 | 5/1996 |
| WO | 2012148472 A2 | 11/2012 |
| WO | 2013144959 A1 | 10/2013 |

*Primary Examiner* — Christian Sevilla

(57) ABSTRACT

Exemplary embodiments describe soft robotic actuators for medical use, such as during surgeries and other medical procedures. According to one embodiment, a soft robotic incision retractor is provided. According to another embodiment, a soft robotic body tissue retractor is provided. The incision retractor and body tissue retractor may be used together, for example by using the incision retractor to hold open an incision while the body tissue retractor manipulates biological matter or an object accessible through the incision. Described embodiments offer the ability to conform to a given space, reduced risk of damage to surrounding structures as compared to traditional retractors, the ability to deliver varying amounts of force, the ability to be made from medically safe materials, and the potential for re-use or disposability.

20 Claims, 17 Drawing Sheets

(56) References Cited

U.S. PATENT DOCUMENTS

| | | | |
|---|---|---|---|
| 2008/0125803 A1* | 5/2008 | Sadamasa | A61B 10/06 606/190 |
| 2010/0292706 A1* | 11/2010 | Dutson | G06F 3/016 606/130 |
| 2013/0116504 A1* | 5/2013 | Scopton | A61B 1/0008 600/104 |
| 2013/0317303 A1* | 11/2013 | Deshmukh | A61B 17/0218 600/202 |

* cited by examiner

SOFT ROBOTIC RETRACTORS

RELATED APPLICATIONS

The present application is a Continuation of U.S. patent application Ser. No. 14/937,554 filed on Nov. 10, 2015, which claims priority to U.S. Patent Application No. 62/079,302, filed on Nov. 13, 2014. The contents of the aforementioned applications are incorporated herein by reference.

FIELD OF THE DISCLOSURE

The disclosure relates generally to the field of robotics and particularly to medical retractors employing soft robotic actuators.

BACKGROUND

Robotics are used in many industries, such as manufacturing, industrial applications, medical applications, and the like. Soft robotics is a developing area of robotics that provides soft, conformal, and adaptive graspers and actuators to enable robots to interact with objects in a similar manner to a human. In particular, such robots are able to manipulate objects in the same manner as a human hand.

Soft robotics have been employed in connection with robotic systems for grasping objects on an assembly line or in a warehouse. For example, if a part is in a bin, on a shelf, a moving belt, or being moved from a shelf to a belt, an end effector may adapt to picking up the object from various directions, such as a "side pick" or a "top down pick." This same grasper may also adapt to varying objects in each task, just as the human hand can.

SUMMARY

Exemplary embodiments apply the concept of soft robotic actuators to the medical field, and more specifically provide soft robotic retractors for use during surgeries and other medical procedures. Soft robotic actuators have a number of advantages, including the ability to conform to a given space, reduced risk of damage to an object being manipulated or to surrounding structures as compared to traditional retractors, the ability to deliver varying amounts of force, the ability to be made from medically safe materials, and the potential for re-use or disposability.

DETAILED DESCRIPTION OF THE PREFERRED EMBODIMENTS

Figure 1A:
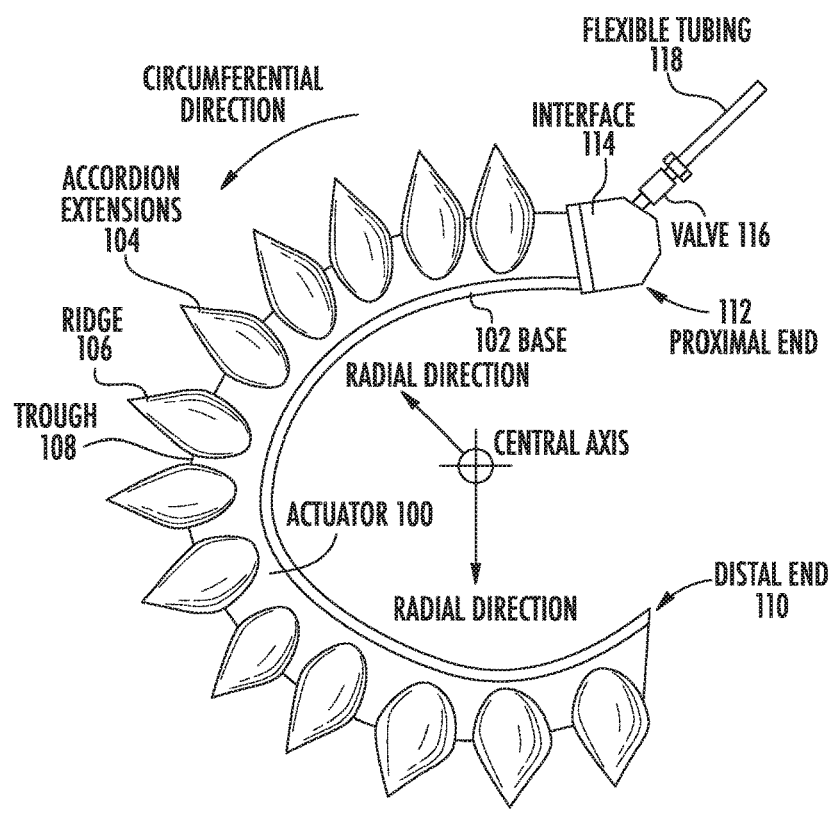
FIGS. 1A-1D depict exemplary incision retractors employing soft robotic actuators.

The present invention will now be described more fully hereinafter with reference to the accompanying drawings, in which preferred embodiments of the invention are shown. The invention, however, may be embodied in many different forms and should not be construed as being limited to the embodiments set forth herein. Rather, these embodiments are provided so that this disclosure will be thorough and complete, and will fully convey the scope of the invention to those skilled in the art. In the drawings, like numbers refer to like elements throughout.

Exemplary embodiments provide soft robotic actuators for medical use, such as during surgeries and other medical procedures. According to one embodiment, a soft robotic incision retractor is provided. According to another embodiment, a soft robotic body tissue retractor is provided. The incision retractor and body tissue retractor may be used together, for example by using the incision retractor to hold open an incision while the body tissue retractor manipulates biological matter or an object accessible through the incision. Described embodiments offer the ability to conform to a given space, reduced risk of damage to surrounding structures as compared to traditional retractors, the ability to delivery varying amounts of force, the ability to be made from medically safe materials, and the potential for re-use or disposability.

A brief overview of soft robotic actuators is now provided.

Soft Robotic Actuators

Conventional robotic grippers or actuators may be expensive and incapable of operating in certain environments where the uncertainty and variety in the weight, size and shape of the object being handled has prevented automated solutions from working in the past. The present application describes applications of novel soft robotic actuators that are adaptive, inexpensive, lightweight, customizable, and simple to use.

Soft robotic actuators may be formed of elastomeric materials, such as rubber. They may be created, for example, by molding one or more pieces of the elastomeric material into a desired shape. Soft robotic actuators may include a hollow interior that can be filled with a fluid, such as air, water, or saline to inflate and actuate the actuator. Upon actuation, the shape or profile of the actuator changes. In the case of an accordion-style actuator (described in more detail below), actuation may cause the actuator to curve or straighten into a predetermined target shape. One or more intermediate target shapes between a fully unactuated shape and a fully actuated shape may be achieved by partially inflating the actuator.

Actuation may also allow the actuator to exert a force on an object, such as an object being grasped or pushed. However, unlike traditional hard robotic actuators, soft actuators maintain adaptive properties when actuated such that the soft actuator can partially or fully conform to the shape of the object being grasped. Moreover, the amount of force applied can be spread out over a larger surface area in a controlled manner. In this way, soft robotic actuators can grip objects without damaging them.

Moreover, soft robotic actuators allow for new types of motions or combinations of motions (including bending, twisting, extending, and contracting) that can be difficult or impossible to achieve with traditional hard robotic actuators.

Exemplary embodiments leverage the advantages of soft robotic actuators to provide retractors suitable for use in medical applications, as discussed below.

Applications

In the medical context, soft robotic actuators have a number of advantages. Soft robotic actuators have the ability to conform to a given space, which means that they can apply a force to tissue or body lumens that may be irregularly sized or difficult to reach. Because soft robotic actuators are conformal and adaptive, and because they can be made from medically safe elastomeric materials, there is a reduced risk of damage to surrounding structures using a soft robotic actuator as compared to traditional retractors. Moreover, soft robotic actuators can deliver varying amounts of force, allowing the retractors to adapt to changing requirements. Still further, because of the wide variety of materials that can be used to make a soft robotic actuator, actuators can be manufactured with the potential for reuse, partial ruse, or disposability, depending on the needs of the user. Still further, because the actuators can change size, they can be passed through small openings (as might be useful, for example, in laparoscopic surgery). After passing through the opening, the actuator may be expanded in size on the far side of the opening to place the actuator in a state in which it can retract or manipulate the target.

Examples of procedures in which soft robotic actuators may be particularly useful include, but are not limited to, open soft tissue management, open surgical adhesiolysis, open surgical appendectomy, open surgical gastric bypass, open surgical cholecystectomy, open surgical esophagogastric fundoplasty, open surgical herniorrhaphy, partial colectomy, complete colectomy, sigmoidectomy, conventional hemorrhoidectomy, open surgical biopsy, intestine transplant, kidney transplant, liver transplant, partial nephrectomy, radical nephrectomy, splenectomy, partial lung resection, lobectomy, open lung biopsy, thoracoscopy procedures, and surgical trauma.

Exemplary soft robotic retractors suitable for use with these (and other) types of procedures are now described.

Exemplary Embodiments

Two types of soft robotic actuators are discussed herein. Incision retractors are designed to be inserted into a location in a body, such as at an incision location or at a location of a wound, and to support the edges of the incision or wound in order to provide a defined working space at the location. Body tissue retractors are designed to be inserted into a working space in a body in order to manipulate biological matter or an object in the working space in order to provide better visual or physical access to a target tissue or organ. For example, a bowel retractor may be used to manipulate a patient's intestines, to move the intestines out of the way during a surgical procedure.

Figure 1B:
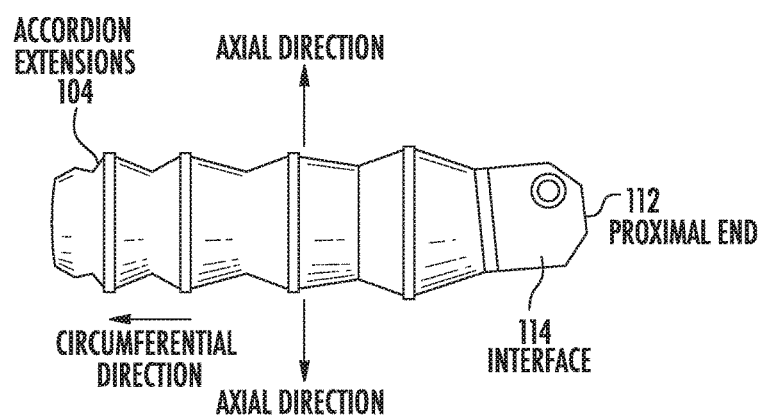
Figure 1C:
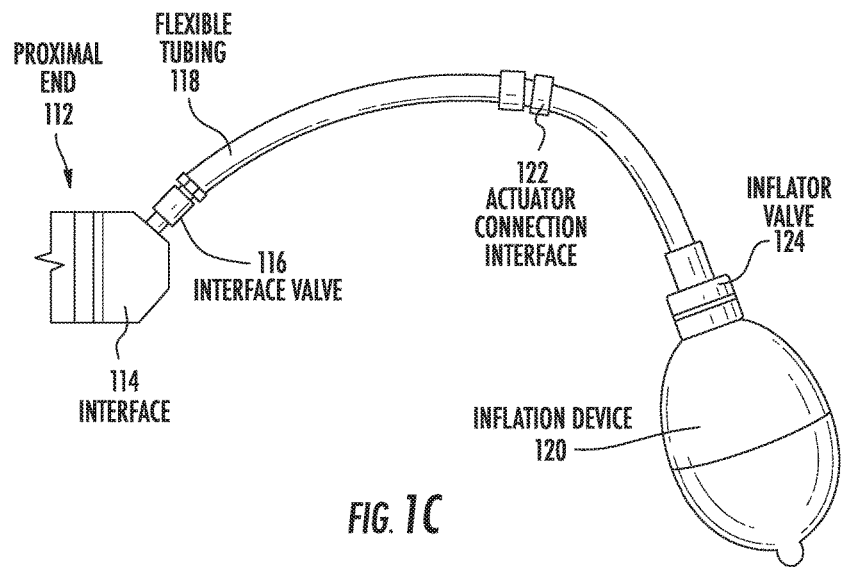
Figure 1D:
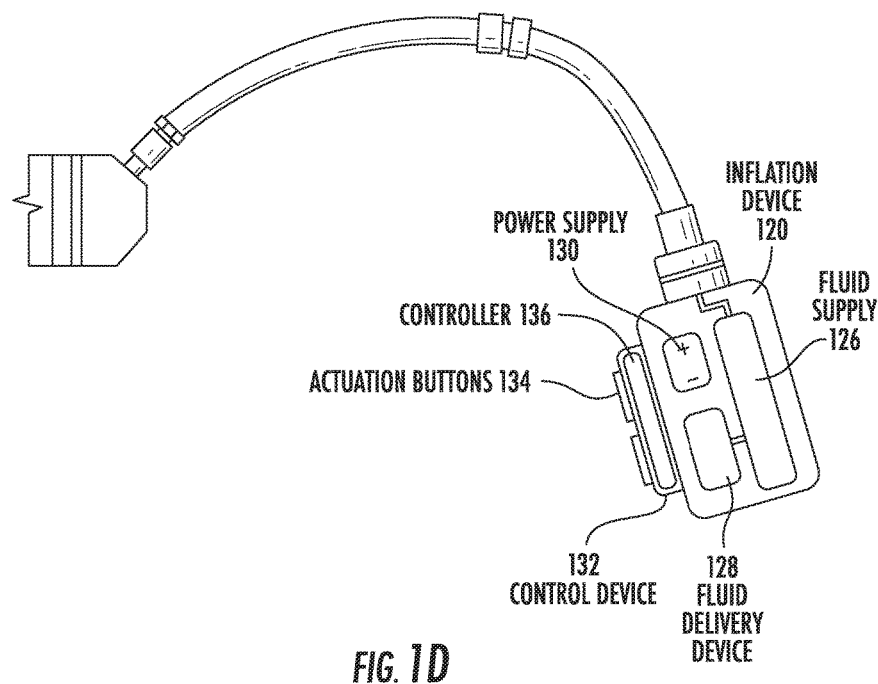

An exemplary incision retractor is depicted in FIGS. 1A-1D. More specifically, FIG. 1A depicts a side view of a portion of the incision retractor that is deployed in an incision. FIG. 1B depicts the portion from FIG. 1A from the top. FIG. 1C depicts a side view of a portion of the incision retractor that is maintained outside of the incision and is manipulated by a user. FIG. 1D depicts an alternative embodiment for the external portion depicted in FIG. 1C.

Although the following description describes these devices as "incision" retractors, one of ordinary skill in the art will recognize that the present invention is not so limited. In addition to providing retraction capabilities at areas of incisions, the exemplary incision retractors described herein can be used to provide retraction capabilities at any suitable location (e.g., intra-abdominal organ retraction).

The incision retractor generally includes a soft robotic actuator 100, which is inflatable with an inflation fluid. The inflation fluid may be provided via an inflation device 120 through flexible tubing 118.

In general, an incision retractor should provide safe, reliable, and maximal physical and visual access to subcutaneous anatomy via an open incision of minimal size. The exemplary incision retractor can be deployed by inflating the soft robotic actuator 100; prior to or following deployment, the soft robotic actuator 100 may be in an uninflated state. When inflated, the actuator 100 has a substantially "C" or partial oval shape; prior to inflation or following deflation, the actuator 100 takes on a relatively flat shape and can be folded, if desired. This allows the retractor to maximize physical and visual access when deployed, while having a minimal profile during insertion into an incision.

In the inflated state, the actuator 100 curves around a central axis, as shown in FIG. 1A. For ease of discussion, several directions are defined herein. An axial direction passes through the central axis, as shown in FIG. 1B. A radial direction extends in a direction perpendicular to the axial direction, in the direction of the radius of the circle formed by the inflated actuator 100. A circumferential direction extends along a circumference of the inflated actuator 100.

In the inflated state, the actuator 100 may exert between 0.1 and 5 pounds of force pounds of force in the radial direction along the circumferential edge of the actuator 100. In some embodiments, the actuator exerts 1 to 3 pounds of force. In one embodiment, the actuator exerts about 1.5 pounds of force.

The amount of force that a given retractor is able to exert may be varied in a number of ways. For example, a larger actuator 100 will deliver more force at the same degree of inflation pressure as compared to a smaller actuator 100. By adding reinforcements to the actuator 100, such as fiber reinforcements, more force can be delivered in the same form factor by being able to operate at a higher pressure. Similarly, by designing the actuator 100 with thin sheets of plastic or relatively stiff elastomers, more force could be delivered with the same sized actuator by utilizing a higher inflation pressure.

The construction of the incision retractor provides sufficient static and dynamic strength to repeatedly retract soft tissues while behaving reliably and predictably under varying external loads (e.g., the retractor does not shift or dislodge under stress). Similarly, the retractor behaves reliably when physically manipulated in the inflated state (without undesirably shifting or dislodging during the manipulation). These benefits occur, in part, because the soft robotic actuator remains relatively conformal when inflated, due to the materials used (e.g., the materials that make up the body of the actuator and the fluid used to inflate the actuator) and the general construction of the device. Because the device is relatively conformal, it takes on the shape of the area in which it is deployed, to a certain degree, and hence can remain relatively stable.

The actuator 100 may be made of one or more elastomeric materials that allow for a relatively soft or conformal construction. The elastomeric materials may be selected from a group of biocompatible or otherwise medically safe, FDA-approved materials. The actuator 100 may incorporate polymers that have drug eluting capabilities or antimicrobial coatings. The actuator 100 may be manufactured in a Good Manufacturing Process ("GMP")-capable facility.

The actuator 100 may include a base 102 that is substantially flat. When inflated, the area inside of the base 102 (i.e., the area radially interior to the base 102) forms the working area through which subcutaneous matter can be manipulated. Because the base 102 is substantially flat whereas the top is not (due to the accordion extensions discussed below), the actuator is inclined to bend in a radially outward direction Moreover, making the base 102 substantially flat provides a relatively large working area as compared to if the base 102 were not flat.

Alternatively, the base 102 may incorporate one or more overmolded slats or other suitable stiff structures to prevent the base from bowing upon pressurization, which may further increase the available work area. The base 102 of a soft actuator can have the tendency to bow away from the neutral bending plane of the actuator during inflation. This bowing of the base 102 increases the second moment of area of the actuator's cross section, thereby increasing the actuator's resistance to bending. This behavior diminishes the function of the actuator 100. This problem can be mitigated by overmolding rigid elements (e.g. plastics, metals, ceramics, or stiffer elastomers) in to the base 102. This is accomplished by placing a plurality of rigid elements into the base 102 where the long axis of each element is oriented perpendicular to the neutral axis of bending. This orientation allows the rigid elements to prevent bowing of the base 102 in the direction perpendicular to the neutral axis but only minimally impedes bending along the neutral axis. By reducing the tendency of the base 102 to bow outwards, the rigid elements may provide an expanded working area.

The actuator 100 may include one or more accordion extensions 104. The accordion extensions 104 allow the actuator 100 to bend or flex when inflated, and help to define the shape of the actuator 100 when in an inflated state. The accordion extensions 104 include a series of ridges 106 and troughs 108. The size of the accordion extensions 104 and the placement of the ridges 106 and troughs 108 can be varied to obtain different shapes or extension profiles.

Although the exemplary incision retractor of FIGS. 1A-1D is depicted in a "C" or oval shape when deployed, one of ordinary skill in the art will recognize that the present invention is not so limited. By changing the shape of the body of the actuator 100, or the size, position, or configuration of the accordion extensions 104, different sizes, shapes, and configurations may be achieved. Moreover, varying the amount of inflation fluid provided to the actuator 100 allows the retractor to take on one or more intermediate sizes or shapes between the un-inflated state and the inflated state. Thus, an individual actuator 100 can be scalable in size and shape by varying inflation amount, and an incision retractor can be further scalable in size and shape by replacing one actuator 100 with another actuator 100 having a different size, shape, or configuration.

The actuator 100 may be repositionable and adjustable intra-operatively. This may enable highly dynamic procedures, such as bowel runs, to be performed.

The actuator 100 extends from a proximal end 112 to a distal end 110. The proximal end 112 connects to an interface 114. The interface 114 allows the actuator 100 to be releasably coupled to other parts of the incision retractor. The interface 114 may be made of a medically safe material, such as Acrylonitrile-Butadiene-Styrene ("ABS") or Delrin. The interface 114 may be releasably coupled to one or both of the actuator 100 and the flexible tubing 118. The interface 114 may have a port for connecting to the actuator 100. Different interfaces 114 may have different sizes, numbers, or configurations of actuator ports, in order to accommodate larger or smaller actuators, different numbers of actuators, or actuators in different configurations.

The actuator 100 may be inflated with an inflation fluid supplied from an inflation device 120 through flexible tubing 118. The interface 114 may include or may be attached to a valve 116 for allowing fluid to enter the actuator 100 but preventing the fluid from exiting the actuator (unless the valve is opened). The flexible tubing 118 may also or alternatively attach to an inflator valve 124 at the inflation device 120 for regulating the supply of inflation fluid at the location of the inflation device 120.

The flexible tubing 118 may also include an actuator connection interface 122 for releasably connecting to the interface 114 at one end and the inflation device 120 at the other end. By separating the two parts of the actuator connection interface 122, different inflation devices 120 may be connected to different interfaces 114 and/or actuators 100.

The inflation fluid may be, for example, air or saline. In the case of air, the inflation device 120 may include a hand-operated bulb, bellows, catheter balloon inflator, or syringe for supplying ambient air. In the case of saline, the inflation device 120 may include a syringe or other appropriate fluid delivery system. Alternatively or in addition, the inflation device 120 may include a compressor or pump for supplying the inflation fluid.

In some applications, saline may be a preferred inflation fluid. For example, in certain applications saline may be superior to air due to the fact that, in the unlikely event that the actuator 100 should rupture or develop a leak, the liquid saline will depressurize the actuator 100 with minimal volume expansion thereby causing less damage to the patient. In contrast, if an actuator 100 containing compressed air ruptures, the air will undergo a significant volume expansion that could injure a patient. In addition, this event could leave air pockets in the patient, which could be dangerous (e.g., if the air pockets were located in the patient's vascular system).

For example, FIG. 1D depicts an alternative inflation device 120. The inflation device 120 includes a fluid supply 126 for supplying an inflation fluid. For example, the fluid supply 126 may be a reservoir for storing compressed air or saline, a cartridge storing pressurized or liquefied gas (such as carbon dioxide), or may be a vent for supplying ambient air to the flexible tubing 118.

The inflation device 120 further includes a fluid delivery device 128, such as a pump or compressor, for supplying inflation fluid from the fluid supply 126 to the actuator 100 through the flexible tubing 118. The fluid delivery device 128 may be capable of supplying fluid to the actuator 100 or withdrawing the fluid from the actuator 100. The fluid delivery device 128 may be powered by electricity. To supply the electricity, the inflation device 120 may include a power supply 130, such as a battery or an interface to an electrical outlet.

The power supply 130 may also supply power to a control device 132. The control device 132 may allow a user to control the inflation or deflation of the actuator, e.g. through one or more actuation buttons 134 (or alternative devices, such as a switch). The control device 132 may include a controller 136 for sending a control signal to the fluid delivery device 128 to cause the fluid delivery device 128 to supply inflation fluid to, or withdraw inflation fluid from, the actuator 100.

Different geographies or business needs may dictate different requirements for the incision retractor. For example, depending on the needs of the user, the incision retractor may be designed to be disposable, reusable, or partially disposable and partially reusable.

For example, the incision retractor as a whole may be disposable. In a disposable configuration, each component of the incision retractor is designed to be a sterile, single-use component. The inflation device 120 may be a hand-operated inflator bulb or bellows. The inflation device 120 may provide a working fluid of air or saline as an inflation fluid.

In this configuration, the incision retractor does not require a large up-front investment of capital, and is relatively easy to use. Moreover, no maintenance is required, as the incision retractor can simply be disposed of after use.

Alternatively, the incision retractor as a whole may be reusable. In this configuration, the components of the retractor (particularly the actuator 100) may be constructed of relatively high-grade materials that are compatible with cleaning in an autoclave. The inflation device 120 may be hand-operated (e.g., an inflation bulb or bellows), or may be electronic (with or without an off-board control device). The inflation device 120 may provide a working fluid of air or saline as an inflation fluid.

In this configuration, although a larger up-front cost may be required, longer-term costs over time may be smaller due to the fact that incision retractors do not need to be replaced after each operation. Moreover, because each retractor is designed for multiple uses, the retractors can be provided with more functionality and durability.

Alternatively, portions of the incision retractor may be designed to be disposable, while other portions are reusable. For example, the inflation device 120 and/or control device 136 may be reusable, while the actuator 100 may be single-use and disposable. The inflation device 120 may provide a working fluid of saline as an inflation fluid.

In some applications, surgeons may require that sufficient tissue perfusion occur at the margins of the incision. Therefore, in order to stimulate tissue perfusion, in some embodiments the retractor may be configured to vibrate or pulse intermittently. For example, the actuator 100 may be provided with a small vibration device powered locally or from the inflation device 120. In these embodiments, the actuator 100 should be sufficiently sturdy so as to maintain the amount of retraction and the shape of the retracted incision. In some embodiments vibration may be achieved with a vibratory motor, and pulsation may be achieved by cyclically modulating pressure (e.g., automatically through a control device or manually through a hand-held inflation device).

The incision retractor may be used in conjunction with a body tissue retractor. Exemplary body tissue retractors are depicted in FIGS. 2A-2D.

The body tissue retractor may be used to manipulate, retract, or sequester body tissue, organs, or objects while reducing the potential for injury, unintended reduction of perfusion, or tissue puncture. This allows surgeons to maximize visual and physical access to target subcutaneous anatomy via an open incision of minimal size. The body tissue retractor is therefore capable of exerting sufficient static and dynamic strength to repeatedly retract soft and sensitive organs.

The body tissue retractor may be operated by hand in some embodiments, but the present invention is not so limited. For example, some or all of the body tissue retractor may be mounted at the end of a robotic arm for the purpose of performing robotic surgery.

Moreover, although the body tissue retractor may be used in conjunction with the above-described incision retractor, the body tissue retractor may additionally or alternatively be used in conjunction with other devices. In one embodiment, the body tissue retractor may be fed through a trocar for the purpose of performing laparoscopic surgery.

Furthermore, due to the relatively compliant nature of the retractor, the retractor is capable of behaving reliably under varying external loads and when the retractor is physically manipulated in an inflated state. In particular, the retractor does not shift or dislodge when manipulated or subjected to external stress.

Moreover, the retractor should apply safe pressures to retracted tissue. This allows surgeons to maximize or maintain the health of retracted tissue.

Figure 2A:
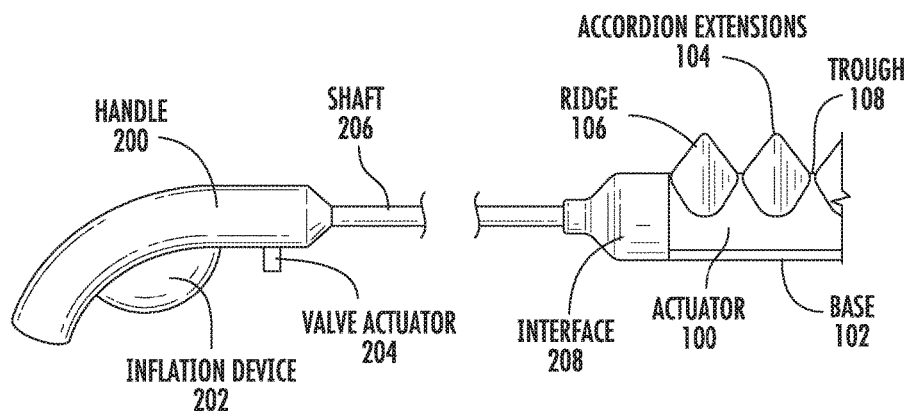
FIGS. 2A-2D depict exemplary body lumen retractors employing soft robotic actuators.

As shown in FIG. 2A, the body tissue retractor includes a handle 200 to allow a user to manipulate the body tissue retractor. The handle may be ergonomically designed for a comfortable grip. The handle 200 may include a hand-operated inflation device 202, such as a bulb or bellows. The inflation device 202 may include one or more valves to allow the inflation device 202 to operate as a hand pump (e.g., a sphygmomanometer bulb). The inflation device 202 of the body tissue retractor may be of similar construction to the inflation device 120 of the incision retractor (including the variations discussed above).

In some embodiments, the body tissue retractor may provide haptic feedback to a user or to a control device. For example, the inflation device 202 may be filled with a predetermined amount of fluid that is confined or trapped in a system made up of the inflation device 202, tubing inside the shaft 206, and the actuator 100. When a user or control device activates the inflation device 202, some of the fluid exits the inflation device 202 and is directed to the actuator 100. At some point, the actuator 100 may make contact with an object, causing the actuator 100 to deflect. When the actuator 100 deflects, an amount of inflation fluid proportional to the amount of deflection is forced back out of the actuator 100, into the tubing, and returns to the inflation device 202. This causes an inflation force to be exerted on the inflation device 202, which allows for an operator or controller to feel the deflection of the actuator 100 directly through a tactile interaction with the inflation device thereby providing haptic feedback. This may allow, for example, a surgeon to feel the degree of tissue retraction that is achieved without the need to use an electronic visualization device, such as a camera, or an expensive haptic robotic feedback device.

The inflation fluid that exits the actuator 100 in response to the deflection may also be measured by one or more sensors, such as a pressure sensor and/or a flow sensor, that are present in the actuator 100, the shaft 206, or the inflation device 202. For example, a flow sensor may measure the flow of the inflation fluid from the actuator 100 back into the inflation device. In another embodiment, the inflation device 202 may be held in a state where its volume is locked. As inflation fluid flows back into the inflation device 202, the overall pressure of the system would increase, which may be measured by a pressure sensor.

The sensor outputs may be read by a controller (e.g., in digital form) and may serve as an input signal that the controller processes to generate haptic feedback. The controller may output a feedback signal proportional to the input signal from the sensor outputs, where the feedback signal causes a haptic device in the handle 200 to generate a haptic output that can be felt by an operator of the handle 200. Alternatively or in addition, the haptic output feedback signal may not be proportional to the input signal. For example, if the force delivered by the retractor approaches a predetermined threshold (e.g., corresponding to a patient pain threshold or a threshold above which damage to the tissue is risked), the output feedback signal may vary non-linearly so that the tactile feedback becomes more intense. This may serve as a warning of impending danger.

In one embodiment these signals could be used to trigger the action of a vibratory motor in the handle 200 in order to provide the user with a tactile indication that the actuators 100 are being deflected.

The handle 200 may also include a valve actuator 204, such as a pin, for allowing a user to open or close a valve that sits in a fluid path between the inflation device 202 and an actuator 100. The valve actuator 204 may be similar to the interface valve 116 or the inflator valve 124 of the incision retractor, discussed above.

The handle 200 may connect to a shaft 206 that extends from the handle 200. The shaft 206 allows the body tissue retractor to reach into an area inside of an incision to manipulate subcutaneous matter.

The shaft 206 also serves as a conduit for routing inflation fluid from the inflation device 202 to the actuator 100. To this end, the shaft 206 may include a flexible elastomeric material to ease assembly of the device. For example, a tube made of rubber or other elastomeric material may be inserted into the hollow center of the shaft 206 in the axial direction. Because the tube is elastomeric, the tube may expand when pulled in the axial direction, and may return to its original size when the pulling force is released. The tube may include an interface at each end, one for attaching to the inflation device 202 and one for attaching to the actuator 100 or the interface 208. By pulling on the tube, the tube may lengthen so that it extends beyond the ends of the shaft 206, which allows the inflation device 202, the interface 208, and/or the actuator 100 to be easily attached. Releasing the pulling force causes the tube to retract back into the shaft. The interfaces at each end of the tube may be configured to sit flush with the ends of the shaft 206 when the tube returns to its unextended state.

The shaft 206 may connect to an interface 208, which may be similar to the interface 114 of the incision retractor. In particular, the interface 114 may support the actuator 100 and allow different types or sizes of actuators, different numbers of actuators, or different configurations of actuators to be attached to the body tissue retractor. For example, although FIGS. 2A-2D depict a body tissue retractor having two actuators, other embodiments may include three or more actuators in various configurations. In one embodiment, an additional actuator may be placed between the two actuators shown in the Figures, in order to change the spread angle between the fingers. Alternatively or in addition, a cable may be provided that is attached to a spring between the fingers. By pulling on the cable, the spread angle between the fingers may be changed. The cable may run from the actuator(s) 100 to the handle 200 so the operator can change the tension on the cable by hand or with a machine/motor, which then has the effect of spreading the actuator(s) 100.

The actuator(s) 100 attached to the interface 208 may be generally similar to the actuators described above in connection with the incision retractor, but may be sized and configured in order to customize the body tissue retractor to a particular application (e.g., manipulating bowel matter).

In the inflated state, the actuator 100 may exert from about 0.1 pounds to 5 pounds of force in the circumferential direction. In some embodiments, the actuator 100 exerts about 0.2 to 2 pounds of force. The inflation characteristics of an exemplary bowel tissue retractor are shown in FIGS. 2C and 2D.

Figure 2B:
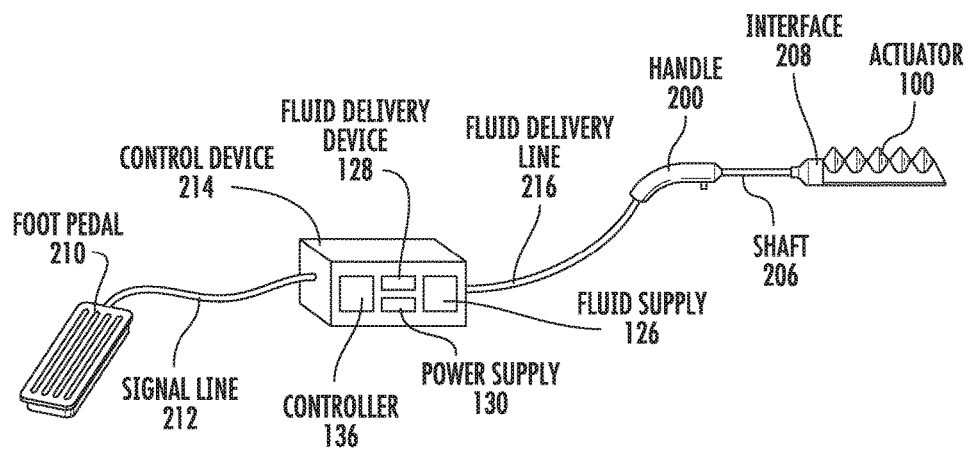
Figure 2C:
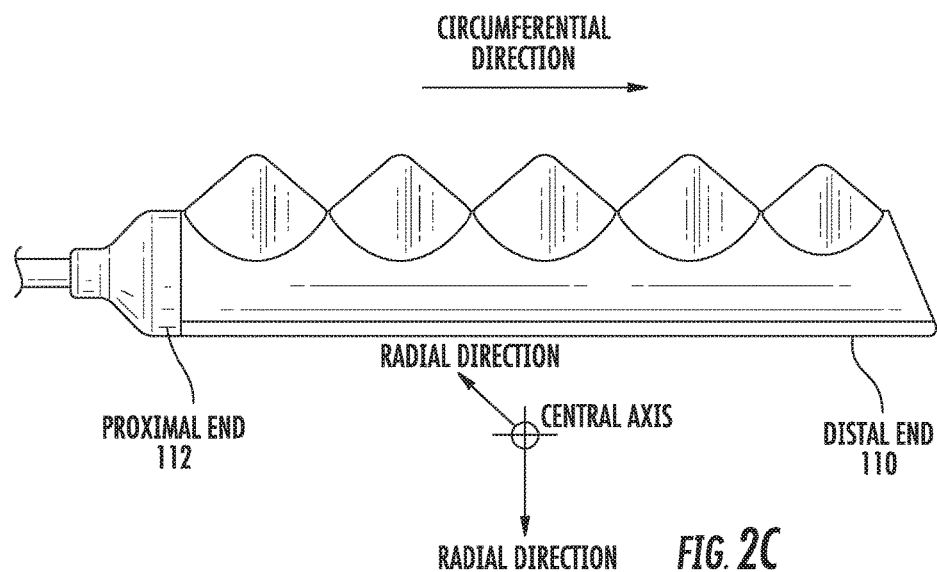
Figure 2D:
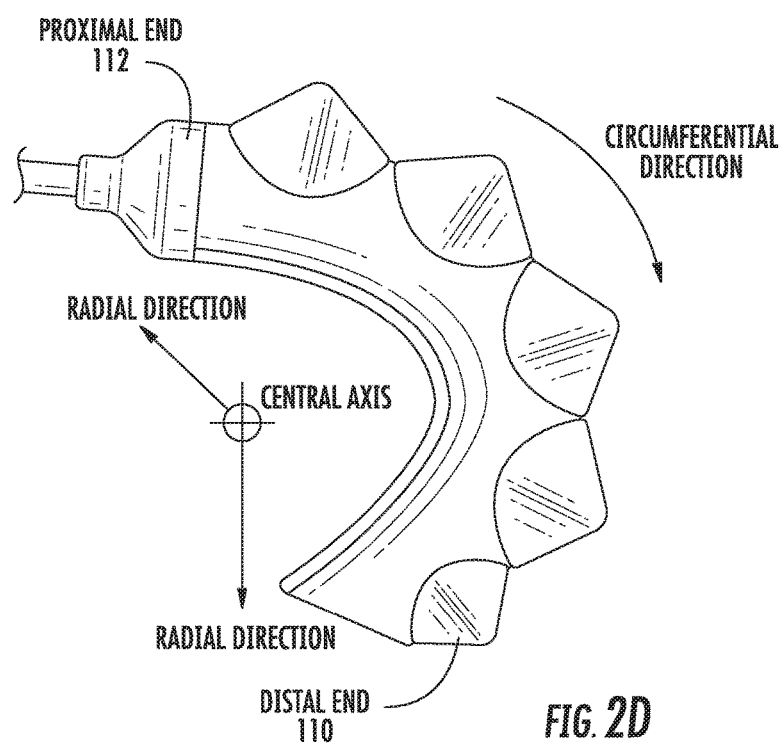

FIG. 2B depicts an alternative inflation mechanism for inflating the actuator 100. The inflation mechanism is operated by a foot pedal 210, which is operable to send a control signal through a signal line 212 to a control device 214. The control device 214 may be configured similarly to the inflation device 120 of FIG. 1D, including a fluid delivery line 216 for providing an inflation fluid from a fluid supply 126 to the handle 200, and from there through the shaft 206 to the actuator(s) 100.

It is noted that the alternative inflation mechanism of FIG. 2B could also be applied to the incision retractor of FIGS. 1A-1D.

As with the incision retractor, the body tissue retractor may be configured to be entirely disposable, entirely reusable, or partially disposable and partially reusable. In the disposable configuration, the shaft 206 may be constructed of aluminum, and the interface 208 may be molded from ABS. The actuator(s) 100 may be constructed of surgical silicone, and the inflation fluid may be air.

In the reusable configuration, the shaft 206 may be constructed of stainless steel, the interface 208 may be molded of Delrin, the actuator may be made of surgical silicone or thermoplastic polyurethane, and the inflation fluid may be saline. Such a body tissue retractor may be deployed with an off-board control system to allow for hand and/or foot pedal control.

In the partially reusable configuration, the body tissue retractor may utilize reusable component materials. The end effector may be made up of an interface 208 made from ABS and disposable actuator(s) 100. The inflation fluid may be saline, and the system may be connected to an off-board control system to enable hand and foot pedal control.

Figure 3A:
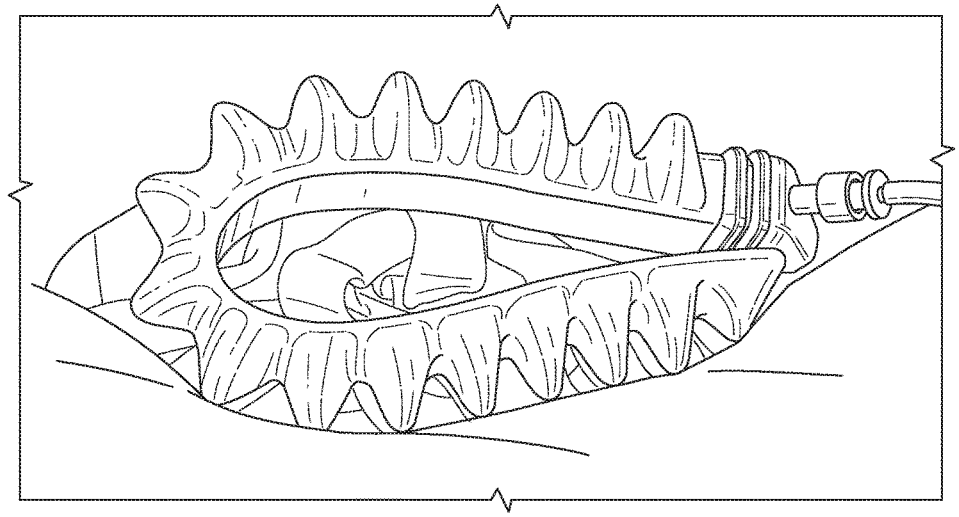
FIGS. 3A-3C depict an example of the exemplary incision retractor and the exemplary body lumen retractor in use.
Figure 3B:
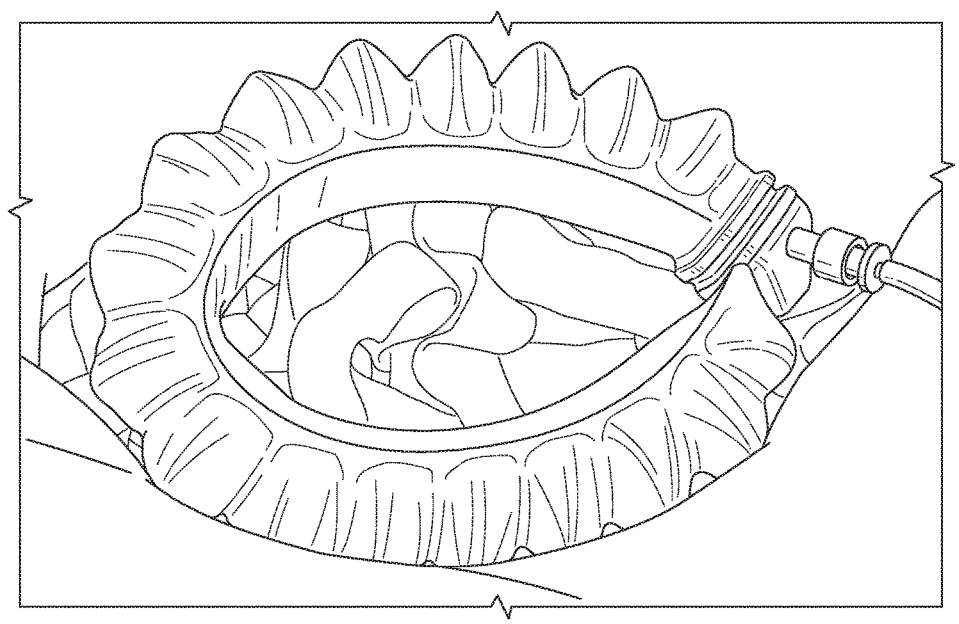
Figure 3C:
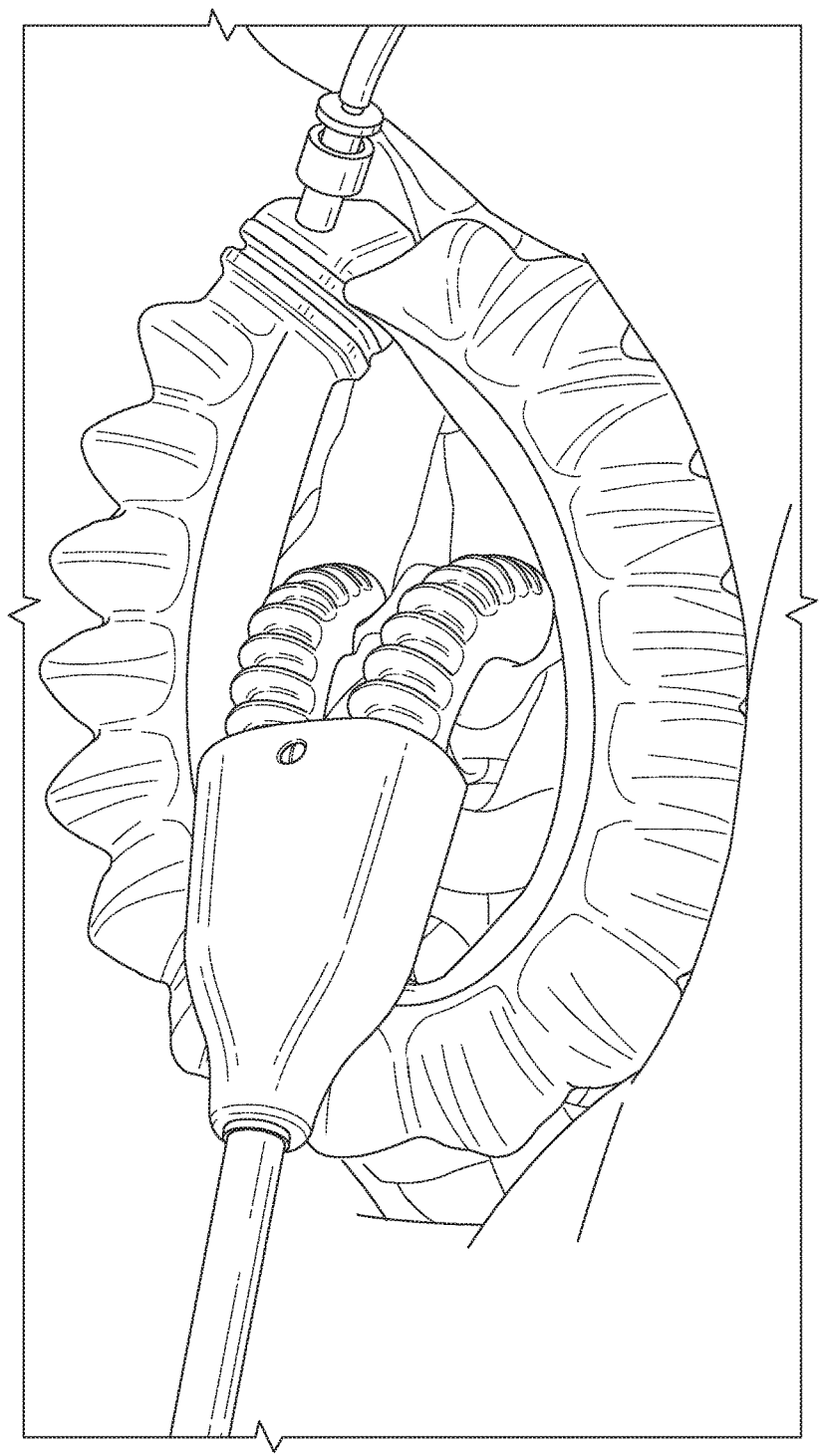
Figure 4A:
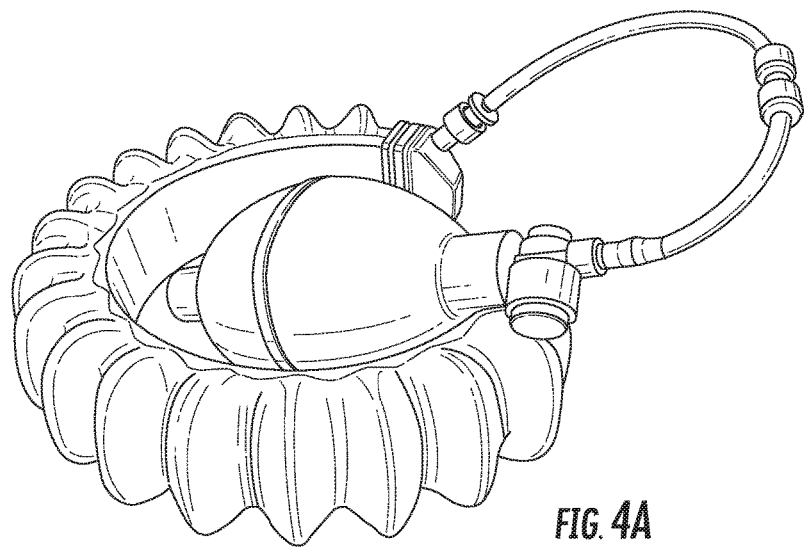
FIGS. 4A-4E are various perspective views showing an exemplary incision retractor in more detail.
Figure 4B:
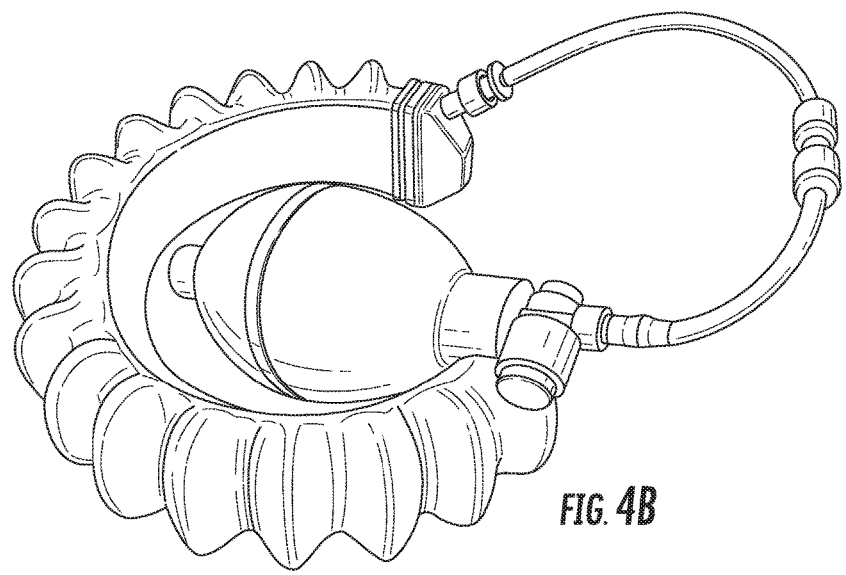
Figure 4C:
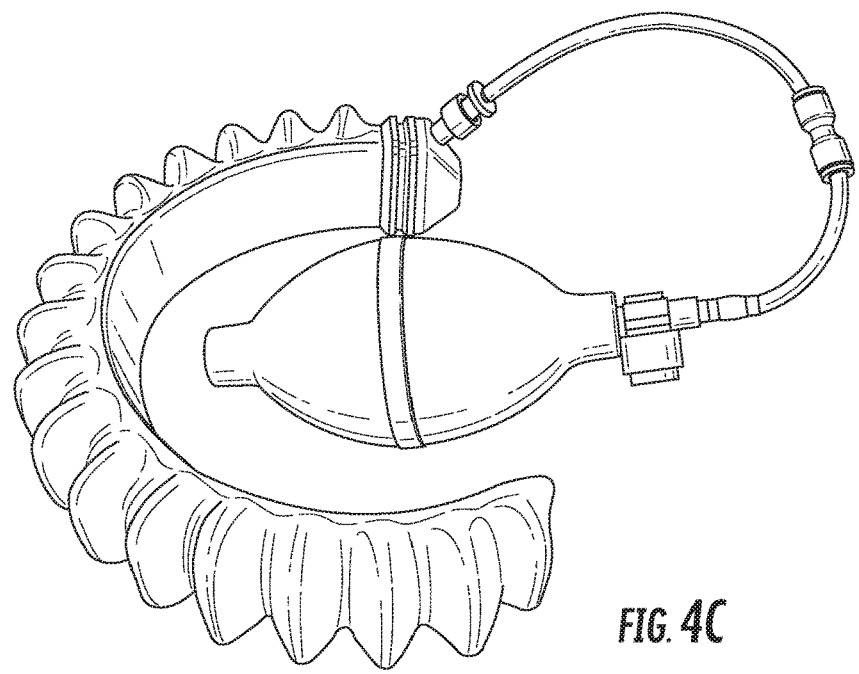
Figure 4D:
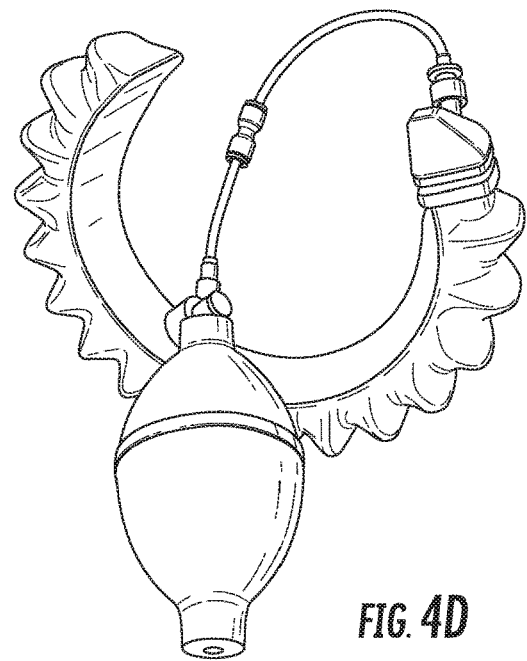
Figure 4E:
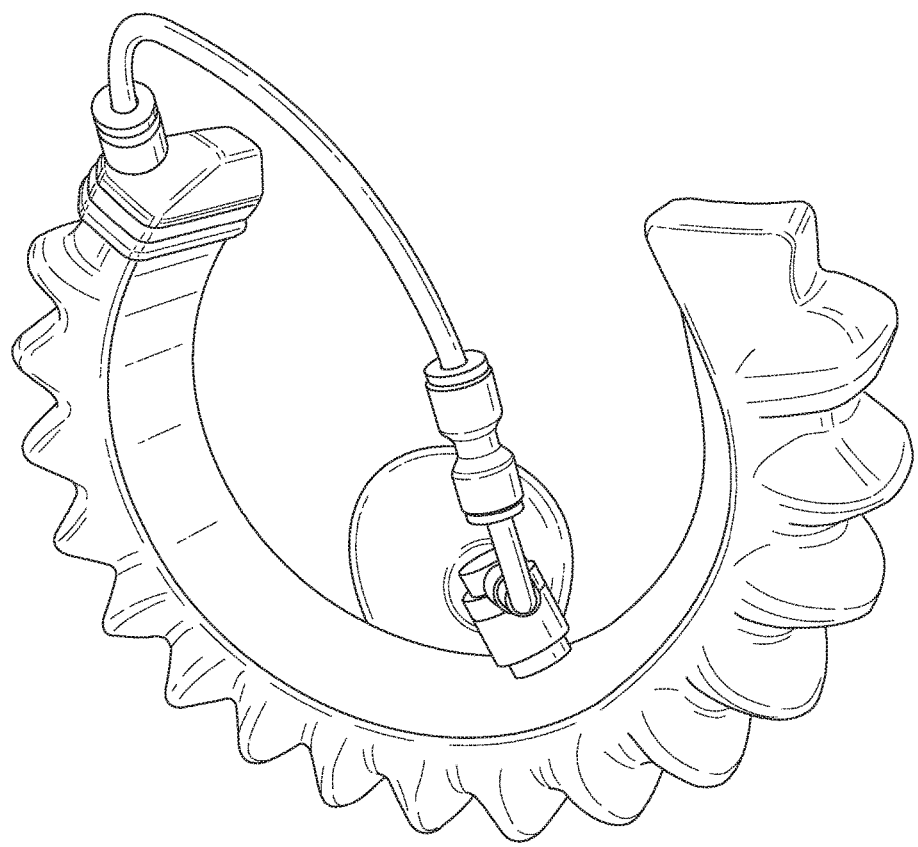
Figure 5A:
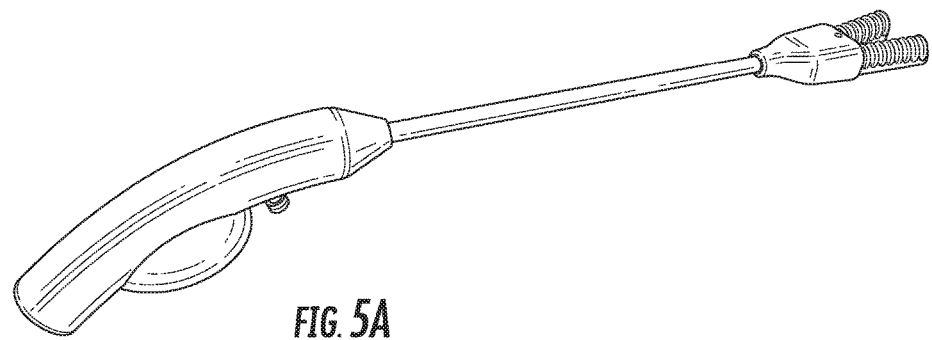
FIGS. 5A-5E are various perspective views showing an exemplary body lumen retractor in more detail.
Figure 5B:
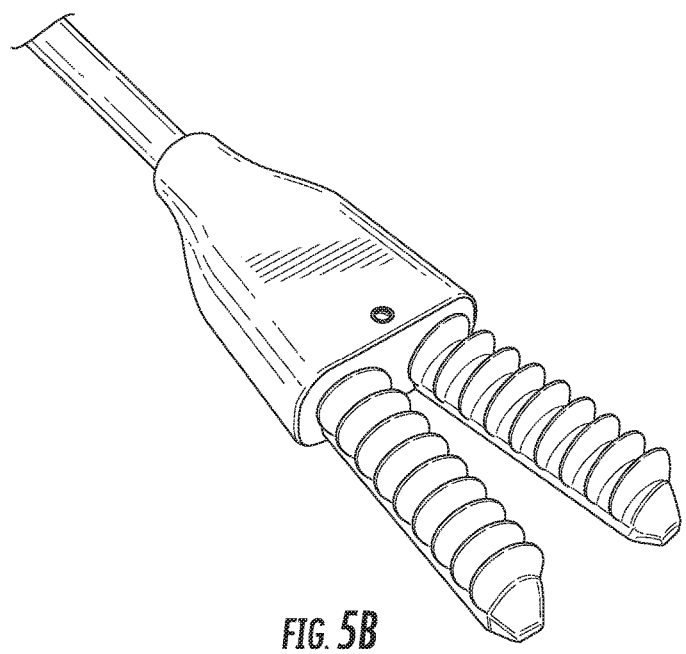
Figure 5C:
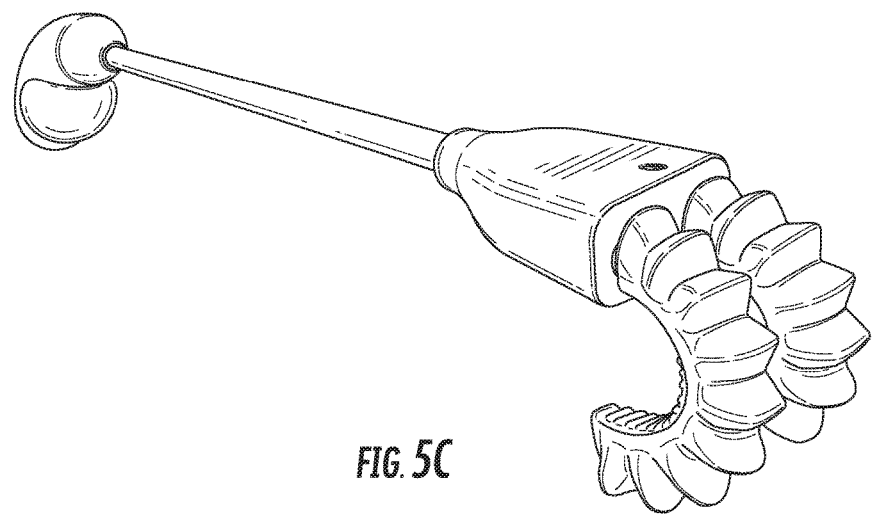
Figure 5D:
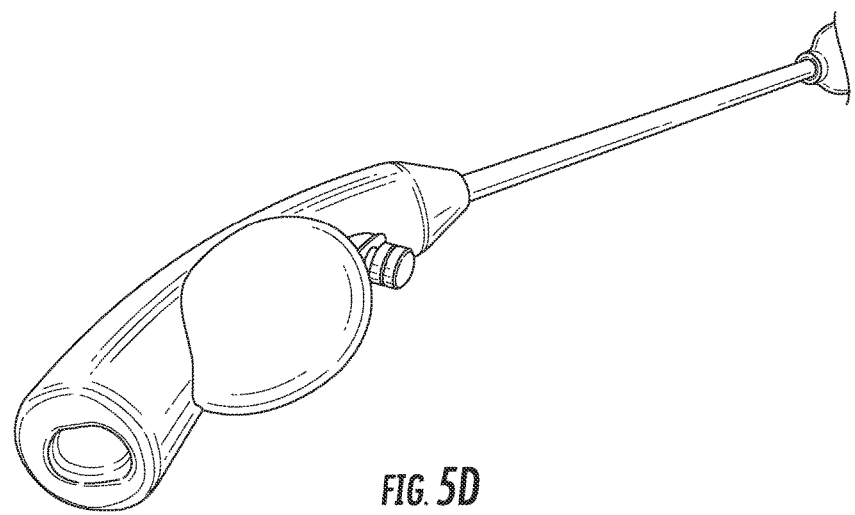
Figure 5E:
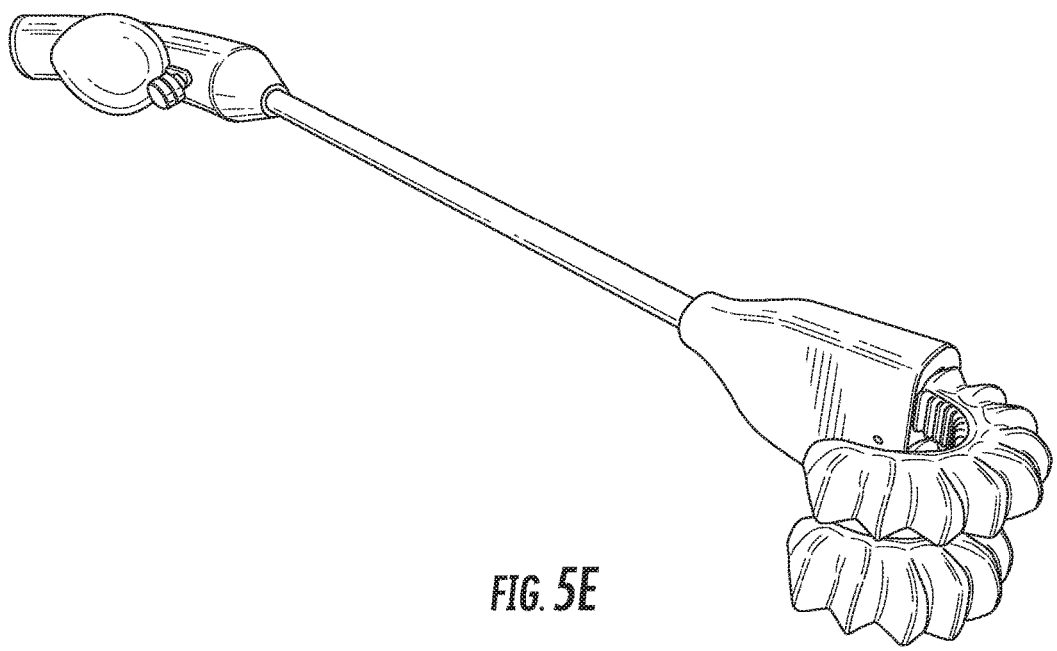

An exemplary use of the incision retractor and the body tissue retractor is shown in FIGS. 3A-3C. FIG. 3A depicts an un-inflated incision retractor in a simulated incision. As shown in FIG. 3A, the un-inflated incision retractor is generally smaller than the area of the incision and can be deployed in a relatively flat configuration (e.g., by folding or bending the actuator 100). As is apparent from FIG. 3A, only a relatively small part of opening created by the incision is accessible through the incision retractor when the actuator is in the un-inflated state.

FIG. 3B depicts the incision retractor after the actuator 100 has been inflated. As shown in FIG. 3B, upon inflation the incision retractor takes on a substantially uniform shape along a length of the actuator from a proximal end to a distal end in a circumferential direction, becoming C-shaped or partially elliptical. As compared to the un-inflated slate shown in. FIG. 3A, the inflated actuator 100 of FIG. 3B allows access to a relatively larger part of the opening created by the incision.

It is noted that the actuator 100 becomes elliptical in shape when deployed in the incision or wound. If the same actuator 100 is inflated in free space, it may take on a substantially circular shape. Because the actuator 100 is configured to take on a substantially circular shape in free space, it exerts an opening force on the non-circular incision, or wound opening when deployed in the incision or wound as it attempts to take on a substantially circular shape. Because an incision is typically a straight line or a non-circular profile, the incised tissue resists the load applied by the actuator 100 as it attempts to achieve a circular state. As the actuator 100 attempts to push itself into a circular state, a load is applied to the resisting tissue which causes the incision to open.

Once the incision is opened using the incision retractor, the body tissue retractor may be inserted into the opening created by the actuator 100, as shown in FIG. 3C. By inflating the actuator(s) of the body tissue retractor, the actuators may take on a relatively more rigid (though still conformal) shape, allowing for the manipulation of body tissue, organs, or objects accessible through the incision.

Further views of the incision retractor and the body tissue retractor are provided in FIGS. 4A-5E. FIGS. 4A-4E depict various perspective views of an exemplary incision retractor, while FIGS. 5A-5E depict various perspective views of an exemplary body tissue retractor, and in particular a soft robotic bowel retractor.

Figure 6:
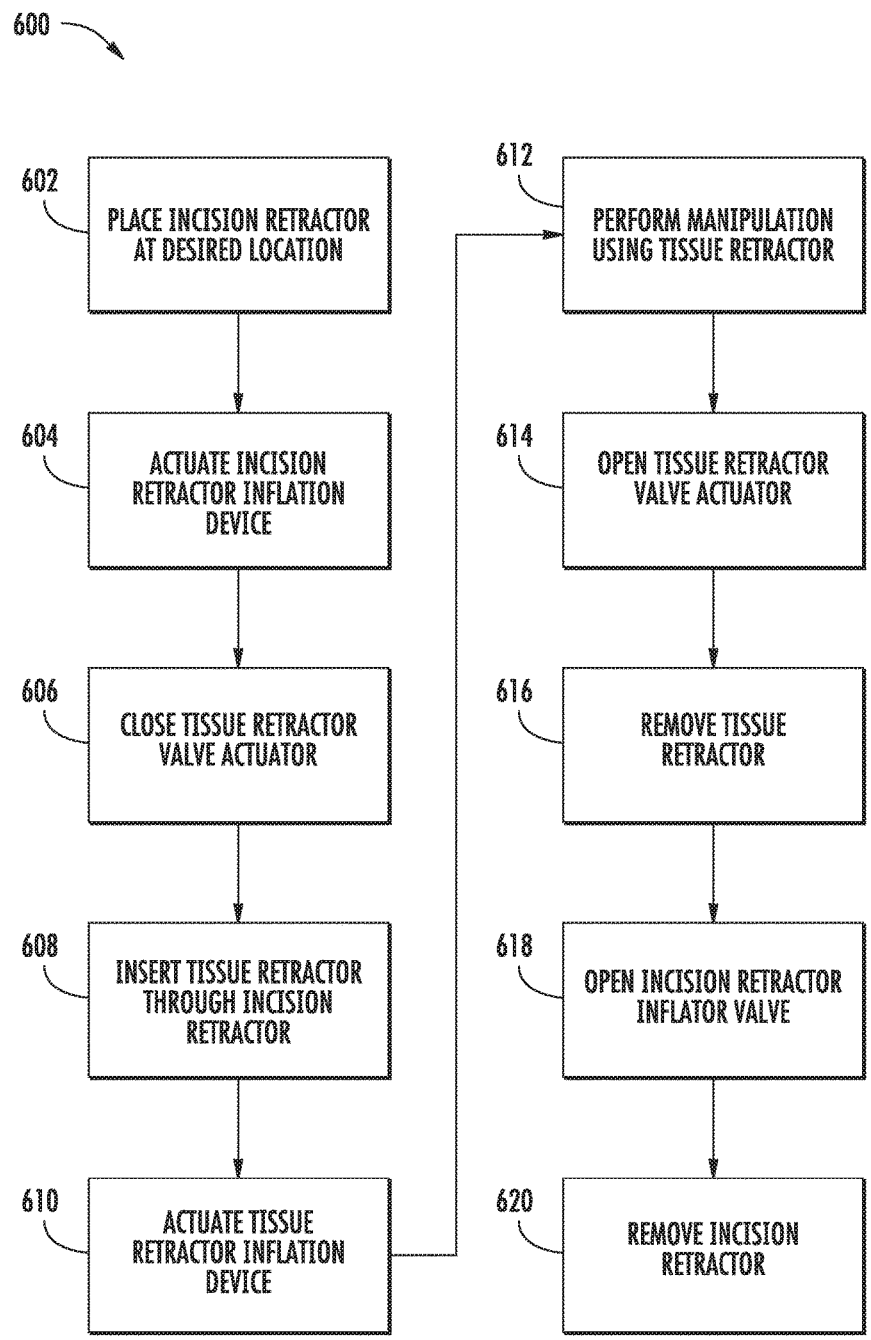
FIG. 6 is a flowchart depicting an exemplary process for using the incision retractor and body lumen retractor.

FIG. 6 is a flowchart 600 describing an exemplary method for using a soft robotic incision retractor in conjunction with a soft robotic body tissue retractor. FIGS. 7A-7H illustrate the steps described in FIG. 6.

Figure 7A:
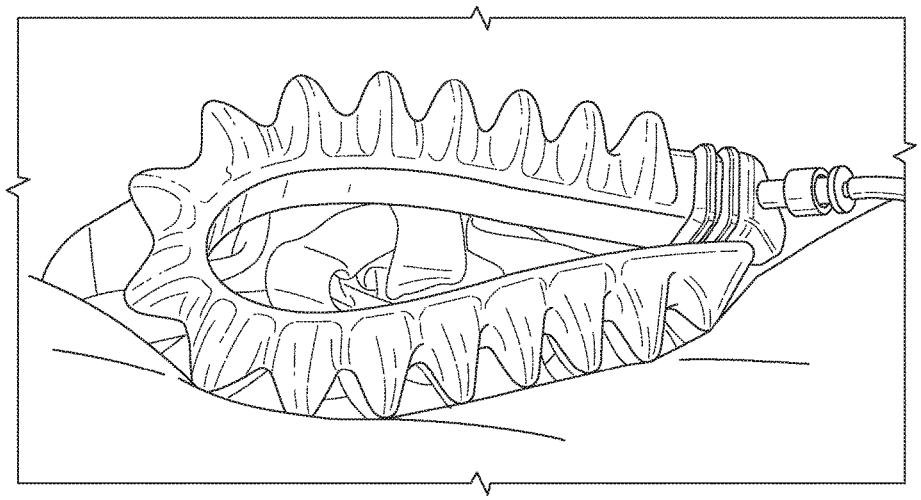
FIGS. 7A-7H depict an exemplary incision retractor and an exemplary body lumen retractor performing the steps described in FIG. 6.

At step 602, the incision retractor may be placed at a desired location. The incision retractor may be in an initially uninflated state, and may be folded or bended in order to allow for easier insertion at the desired location. The location may be, for example, inside of an incision or wound. An example of placing the incision retractor at such a location is shown in FIG. 7A.

Figure 7B:
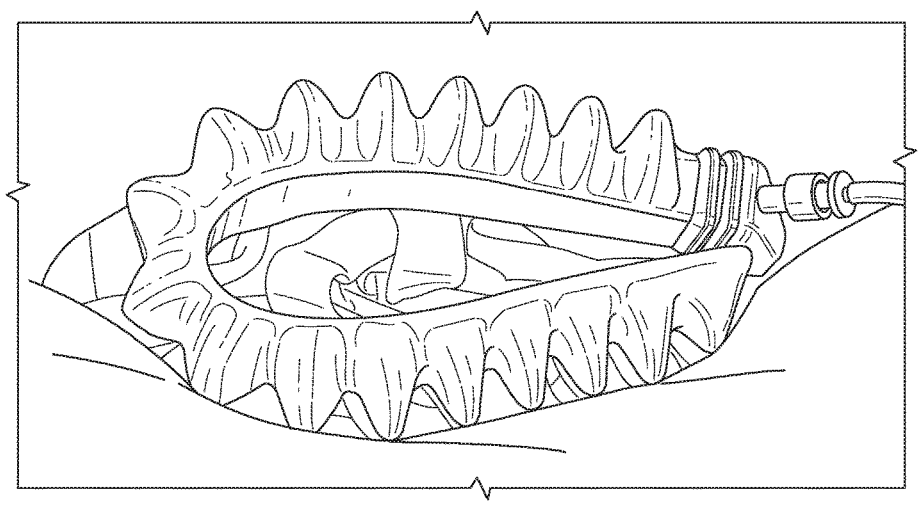
Figure 7C:
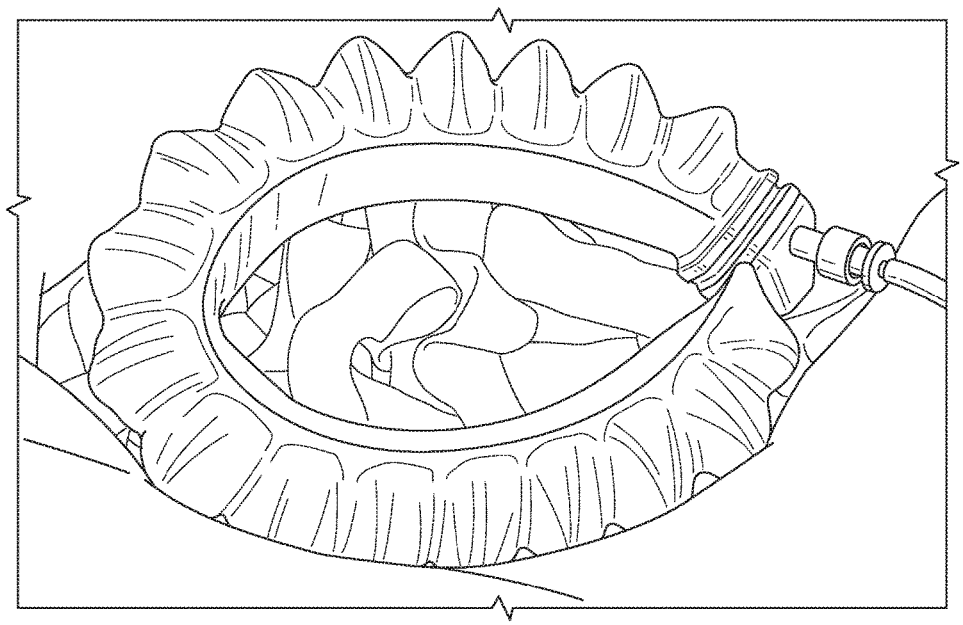

At step 604, the incision retractor inflation device may be actuated. A user may trigger actuation by actuating an inflation device 120, or pressing an actuation button 134 to send a control signal to a fluid delivery device 128. The incision retractor's actuator may undergo inflation as a result of actuation. The actuator may enter an intermediate partially inflated state, as shown in FIG. 7B, before it becomes fully inflated, as shown in FIG. 7C. Depending on the application and the needs of the user, the actuator may be left in the partially inflated state, or may be fully inflated.

At step 606, the tissue retractor valve actuator may be closed. Closing the tissue retractor valve actuator allows for one-way communication of the inflation fluid into the tissue retractor actuator(s), without allowing inflation fluid to exit the tissue retractor actuator(s). For example, if the tissue retractor valve actuator is a pin, the pin may be rotated into a closed position.

Figure 7D:
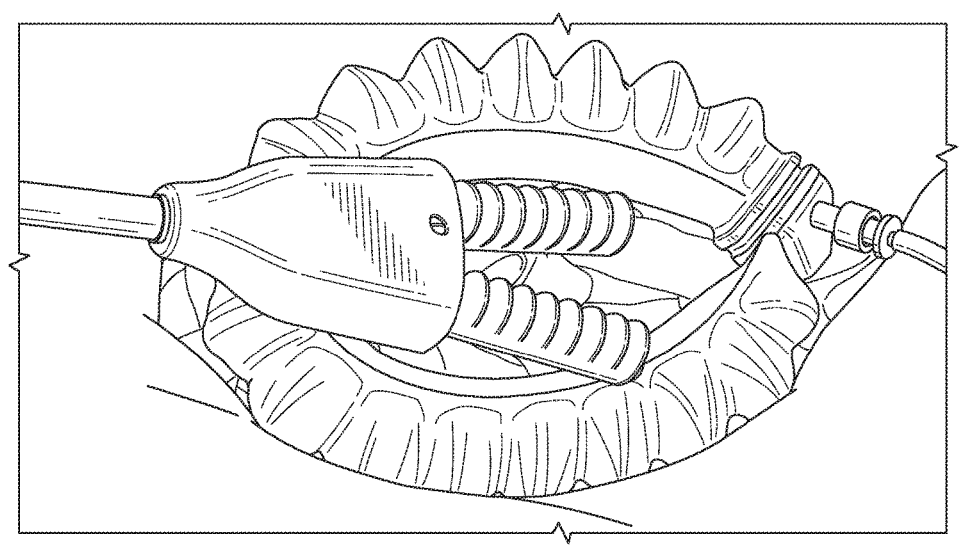

At step 608, the tissue retractor may be inserted through the opening in the incision retractor. The tissue retractor may be in an initially uninflated state, as shown in FIG. 7D.

Figure 7E:
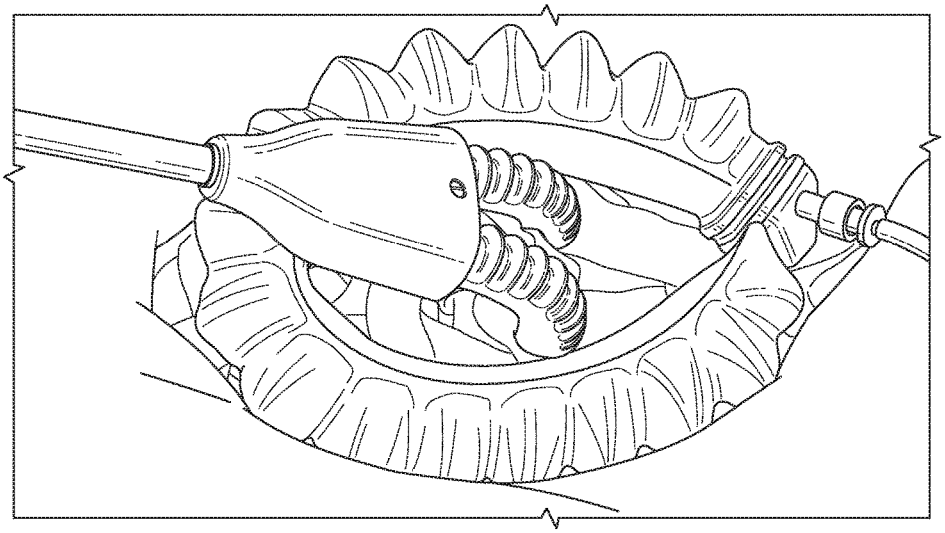
Figure 7F:
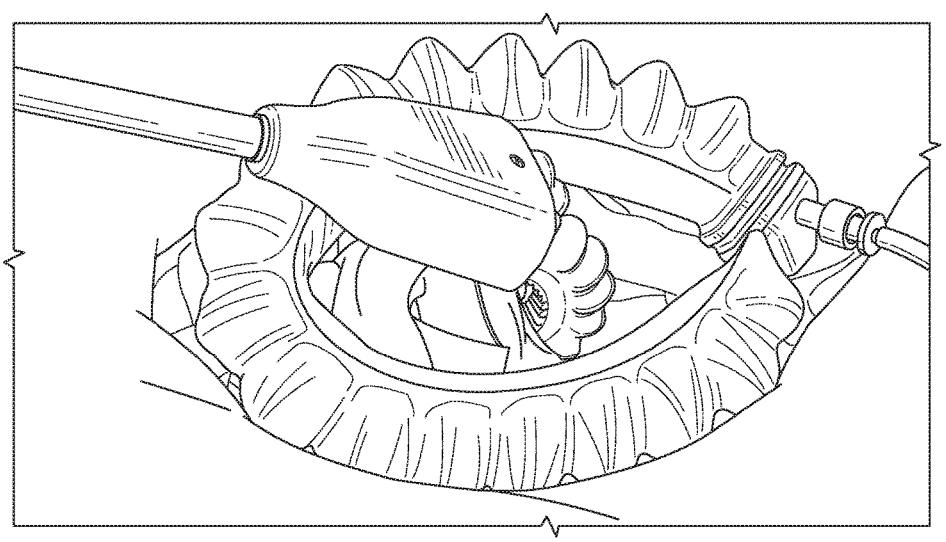

At step 610, the tissue retractor inflation device may be actuated. A user may trigger actuation by actuating an inflation device 202, or pressing an actuation button 134 or actuation pedal 210 to send a control signal to a fluid delivery device 128. The tissue retractor's actuator(s) may undergo inflation as a result of actuation. The actuator may enter an intermediate partially inflated state, as shown in FIG. 7E, before it becomes fully inflated, as shown in FIG. 7F. Depending on the application and the needs of the user, the actuator may be left in the partially inflated state, or may be fully inflated.

Figure 7G:
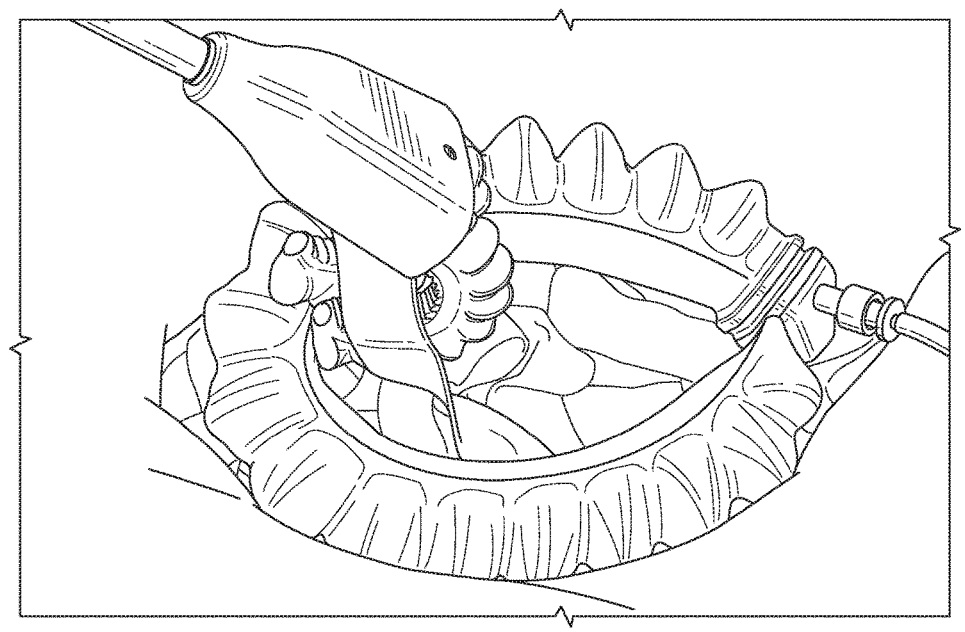

At step 612, a manipulation may be performed using the actuator(s) of the tissue retractor. For example, the tissue retractor may be used to move subcutaneous material out of the way so that a surgeon can access a physical space that would otherwise be blocked. FIG. 7G depicts a simulated example of performing a manipulation with the tissue retractor.

At step 614, the tissue retractor valve actuator may be opened. This allows the inflation fluid to be evacuated from the tissue retractor actuator(s), causing the actuator(s) to enter an uninflated state.

Figure 7H:
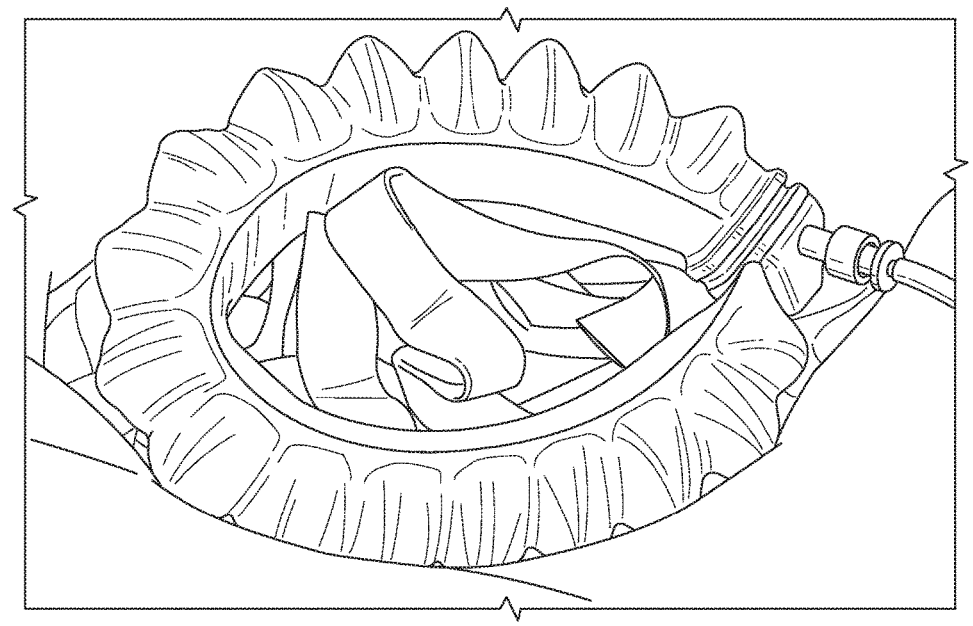

At step 618, the tissue retractor may be removed from the area of the incision held opened by the incision retractor, as shown in FIG. 7H.

At step 620, the incision retractor may be removed. Step 620 may involve opening one or more valves attached to the incision retractor to allow inflation fluid to escape the actuator of the incision retractor. When the retractor has returned to an uninflated state, the incision retractor may be removed from the area of the incision. The incision may now be closed, e.g. by suturing the incision.

By using the devices and techniques herein, medical procedures and surgeries can be provided in a safe and efficient manner, at reduced cost and with a reduced risk of damage to a patient's tissue.

NOTE ON TERMINOLOGY

As used herein, an element or step recited in the singular and proceeded with the word "a" or "an" should be understood as not excluding plural elements or steps, unless such exclusion is explicitly recited. Furthermore, references to "one embodiment" of the present invention are not intended to be interpreted as excluding the existence of additional embodiments that also incorporate the recited features.

While the present invention has been disclosed with reference to certain embodiments, numerous modifications, alterations and changes to the described embodiments are possible without departing from the sphere and scope of the present invention, as defined in the appended claim(s). Accordingly, it is intended that the present invention not be limited to the described embodiments, but that it has the full scope defined by the language of the following claims, and equivalents thereof.

The invention claimed is:

1. A method comprising:
   placing a soft robotic actuator in an uninflated state at a target location proximal to a target incision or wound, the soft robotic actuator comprising a plurality of accordion extensions extending outwards in a radial direction, wherein the soft robotic actuator is sized and configured based on a size and configuration of the target incision or wound, such that in the uninflated state the soft robotic actuator is insertable into the target incision or wound;
   actuating the soft robotic actuator by providing inflation fluid to the soft robotic actuator to exert a force on a periphery of the target incision in the radial direction to hold the target incision or wound in an open state; and
   performing tissue manipulation through the target incision or wound.

2. The method of claim 1, further comprising folding or bending the soft robotic actuator for insertion into the target incision or wound.

3. The method of claim 1, wherein actuating the soft robotic actuator comprises operating a hand-operated inflation bulb, catheter balloon inflator, or syringe.

4. The method of claim 1, wherein actuating the soft robotic actuator comprises triggering a control signal to instruct a control device to inflate the soft robotic actuator.

5. The method of claim 4, wherein the control device comprises one or more pumps, compressors, or regulators for supplying the inflation fluid from a reservoir or an ambient environment, and the control signal causes the one or more pumps, compressors, or regulators to activate.

6. The method of claim 1, further comprising stopping inflation of the soft robotic actuator when the soft robotic actuator is exerting a force of about 1 to 3 pounds on the periphery of the incision or wound.

7. The method of claim 1, further comprising stopping inflation when the soft robotic actuator is in a fully inflated state.

8. The method of claim 1, further comprising stopping inflation when the soft robotic actuator is in a partially inflated state.

9. The method of claim 1, further comprising disconnecting the actuator from an interface, the interface allowing the actuator to be releasably coupled to flexible tubing for supplying the inflation fluid.

10. The method of claim 1, further comprising triggering the actuator to vibrate or pulse intermittently to stimulate tissue perfusion.

11. A method comprising:
inserting a soft robotic actuator in an uninflated state into a target incision or wound, the soft robotic actuator comprising a plurality of accordion extensions extending outwards in a radial direction, wherein the soft robotic actuator is sized and configured so that, in the uninflated state, the soft robotic actuator is insertable into a target incision;
actuating the soft robotic actuator to transition the soft robotic actuator into an inflated state after the soft robotic actuator is inserted into the target incision or wound, wherein in the inflated state the soft robotic actuator becomes relatively more rigid, the rigidity of the soft robotic actuator configured to allow body tissue to be manipulated in the inflated state; and
manipulating the body tissue with the soft robotic actuator.

12. The method of claim 1, further comprising feeding the actuator through a trocar before actuating the soft robotic actuator.

13. The method of claim 11, further comprising stopping inflation of the soft robotic actuator when the soft robotic actuator exerts a force of about 0.2 to 2 pounds on the body tissue.

14. The method of claim 11, wherein actuating the soft robotic actuator comprises operating a hand-operated inflation bulb, catheter balloon inflator, or syringe.

15. The method of claim 11, wherein actuating the soft robotic actuator comprises operating a foot-operated inflator.

16. The method of claim 11, wherein actuating the soft robotic actuator comprises triggering a control signal to instruct a control device to inflate the soft robotic actuator.

17. The method of claim 16, wherein the control device comprises one or more pumps, compressors, or regulators for supplying the inflation fluid from a reservoir or an ambient environment, and the control signal causes the one or more pumps, compressors, or regulators to activate.

18. The method of claim 11, further comprising providing haptic feedback for controlling an amount of force exerted by the soft robotic actuator.

19. The method of claim 11, wherein manipulating the body tissue comprises moving subcutaneous material to provide access to a blocked physical space.

20. The method of claim 11, further comprising de-actuating the actuator by removing some of the inflation fluid after manipulating the tissue, and removing the actuator from the target incision or wound when the actuator is in the uninflated state.

* * * * *